United States Patent [19]

Kross

[11] Patent Number: 4,649,046

[45] Date of Patent: Mar. 10, 1987

[54] AIR FRESHENER

[75] Inventor: Robert D. Kross, Bellmore, N.Y.

[73] Assignee: Hydro Optics, Inc., Hackensack, N.J.

[21] Appl. No.: 625,189

[22] Filed: Jun. 28, 1984

Related U.S. Application Data

[63] Continuation of Ser. No. 361,048, Mar. 23, 1982, abandoned, which is a continuation of Ser. No. 934,224, Apr. 15, 1978, abandoned, which is a continuation of Ser. No. 740,151, Nov. 8, 1976, abandoned, which is a continuation-in-part of Ser. No. 567,894, Apr. 14, 1975, abandoned, which is a continuation-in-part of Ser. No. 432,068, Jan. 9, 1974, Pat. No. 3,877,431.

[51] Int. Cl.$^4$ .................. A61K 31/74; A61K 31/78; A61L 9/01
[52] U.S. Cl. ........................ 424/76; 424/78; 424/81
[58] Field of Search .................. 424/76, 78, 81

[56] References Cited

U.S. PATENT DOCUMENTS

| | | | |
|---|---|---|---|
| 3,253,985 | 5/1966 | Seymour | 424/81 |
| 3,520,449 | 7/1970 | Shepherd et al. | 260/857 |
| 3,566,874 | 3/1971 | Shepherd et al. | 424/81 |
| 3,567,118 | 3/1971 | Shepherd et al. | 424/81 |
| 3,574,822 | 4/1971 | Shepherd et al. | 424/81 |
| 3,576,760 | 4/1971 | Gould et al. | 424/76 |
| 3,577,512 | 5/1971 | Shepherd et al. | 424/81 |
| 3,607,848 | 9/1971 | Stoy et al. | 424/81 |
| 3,655,129 | 4/1972 | Seiner | 239/60 |
| 3,660,563 | 5/1972 | Gould et al. | 424/81 |
| 3,767,787 | 10/1973 | Segal | 424/76 |
| 3,876,761 | 4/1975 | Shepherd | 424/81 |
| 3,886,125 | 5/1975 | Chromecek | 424/76 |
| 3,941,858 | 3/1976 | Shepherd et al. | 260/885 |

FOREIGN PATENT DOCUMENTS 1745187 3/1972 Fed. Rep. of Germany .
2608533 9/1976 Fed. Rep. of Germany .
1205764 7/1967 United Kingdom .

*Primary Examiner*—Allen J. Robinson
*Attorney, Agent, or Firm*—Kenyon & Kenyon

[57] ABSTRACT

An improved polymeric material containing volatilizable active ingredients such as air fresheners, odorants, insecticides and the like, which is clear and can be molded into various transparent tinted or untinted decorative objects, and which can also (if desired) be made flexible and tacky on the surfaces to permit its being readily and inconspicuously adhered to any convenient surface, and which gradually releases the active ingredient into the surrounding atmosphere. The polymeric materials of the invention comprise polymerized hydroxy alkyl esters of vinylically unsaturated carboxylic acids, one or more volatilizable active ingredients, and a solubilizing agent having an appropriate balance of hydrophilic and lipophilic functions selected to substantially dissolve the active ingredient. To avoid premature volatilization and/or destruction of the fragrances and freshening agents preferably employed as active ingredients, the compositions of the invention are prepared by polymerizing the monomer in the presence of the other ingredients at temperatures below those normally required to initiate polymerization. This is accomplished by using a reducing agent in combination with the primary catalyst, preferably (in order to avoid odoriferous or otherwise objectionable residues) an organic water soluble reducing agent in combination with a hydrogen peroxide or (except in low water systems) a persulfate catalyst.

3 Claims, 2 Drawing Figures

AIR FRESHENER

CROSS REFERENCE TO RELATED APPLICATIONS

This application is a continuation of application Ser. No. 361,048, filed Mar. 23, 1982, now abandoned, which is a continuation of application Ser. No. 934,224, filed Apr. 15, 1978, now abandoned, which is a continuation of application Ser. No. 740,151, filed Nov. 8, 1976, now abandoned which is a continuation-in-part of copending application Ser. No. 567,894, filed Apr. 14, 1975 and now abandoned, which in turn is a continuation-in-part application of Ser. No. 432,068, filed Jan. 9, 1974, now U.S. Pat. No. 3,877,431.

BACKGROUND OF THE INVENTION

1. Field of the Invention

This invention relates generally to active agent-containing polymeric materials which slowly release active agents, such as air fresheners, odorants, insecticides, insect repellants and the like, into the surrounding atmosphere, especially into room air, and to the process of preparing these materials.

More particularly, the invention relates to room air freshener products designed to gradually release the active agent into the air over sustained periods. The invention provides improved polymeric materials which gradually dispense the active agent, and which are clear and transparent, and if desired, can be made flexible and tacky at the surface. These properties permit the polymeric materials of this invention to be rolled and marketed in an assortment of convenient forms, such as in sheets or a strip dispenser from which the user can cut or tear off a portion which can then be readily and inconspicuously adhered to any convenient surface in a room. The active air freshener or odorant agent is then gradually released into the room over a sustained period, after which the material can be easily removed and replaced by fresh piece.

In the alternative, the polymeric materials of this invention can be made more rigid and, though clear, can be tinted and formed into, or made a part of, various decorative objects, such as pomanders, mobiles and artificial flowers and the like. For example, the polymeric materials of this invention can be used for the buds or petals of a flower, so that only these parts need be replaced when the active agent is exhausted.

2. Description of the Prior Art

It is well known that air fresheners, odorants, insecticides, insect repellants, and similar agents may be added to a room atmosphere for comfort, health, or other reasons, and the established marketability of such products has led to an ongoing search for improved vehicles for dispensing the active agents into the air.

Products which provide only for repeated instantaneous application, such as by aerosol dispensing means, are suitable for certain purposes, but are of limited usefulness where it is desired to provide continuous release of the active agent into a room atmosphere, and accordingly, there has been a recognized need to provide products which continuously and gradually release their active agents into the atmosphere while unattended.

Heretofore, air freshener products which automatically and gradually release the active agent into the air, have typically comprised bulky dispensers of various types containing only a small amount, e.g., a few percent, of active ingredient which, even if disguised as various objects or fixtures, are apt to be unnecessarily costly and often not as attractive as desired. The advantages of a clear, less bulky and completely inconspicuous material containing high levels of the active air freshener agent within the material itself e.g., from 5 to 20%, and in some cases as much as 50%, and which gradually and continuously releases the active air freshening ingredient into the surrounding atmosphere are thus apparent.

It is known that some types of polymeric materials can be used to entrap various ingredients within the polymer matrix, and that such ingredients can then be released gradually over sustained periods under certain conditions, such as in response to moisture in the case of hydrophilic polymers, and this has led to proposals to employ such polymers as vehicles for various active ingredients. For example, it has been proposed that polymers in the form of powders and films containing active agents which are nonsolvents in the polymer be incorporated into paints and wood treatments and the like, so that the nonsolvent agents form bubbles which gradually reach the surface to be released into the air (e.g., Seiner, U.S. Pat. No. 3,655,129). After the active agent has been exhausted in such films, however, the film itself, which is opaque, remains on the surface to which it has been applied, which limits the usefulness of such techniques to applications or locations, such as closets, where the treated surface can be repeatedly repainted or sprayed with the material, without concern for continuing accumulation of the film.

In applications where it is desired to release the active agent in response to moisture, it has been proposed to use hydrophilic polymers which, when ground into powders, can be mixed with various ingredients to be thereafter released and replaced by the water drawn into the hydrophilic polymer (e.g., Shepard and Gould, U.S. Pat. No. 3,520,949, Examples 15a and 15b). Such mixtures can also be incorporated into the form of sprays or films for application to clothing, bandages, and similar materials (e.g., Shepard and Gould, U.S. Pat. No. 3,657,118). Similarly, if the hydrophilic polymer itself is made water soluble, the untrapped agent can be released upon dissolution of the polymers in water, such as in soaps, detergents, or similar applications (e.g., Gould and Shepard, U.S. Pat. No. 3,681,248 and U.S. Pat. No. 3,772,215). But these techniques are not suitable where it is desired that the active ingredient be gradually and continuously released without depending upon moisture as a primary means to activate or control the rate of release.

Moreover, previous proposals for polymeric vehicles for active agents employed as powders and sprays cannot be conveniently and inconspicuously applied in any desired location and then readily removed after the active agent is exhausted, unless by washing in the case of water soluble materials. Furthermore, even if a suitable hidden surface can be found where continued build up of the material will remain unnoticed, the inconvenience of repeatedly applying such products as paints, coatings or sprays, in such hidden locations, as well as the even greater inconvenience of occasional washing to remove them, remains a disadvantage.

SUMMARY OF THE INVENTION

The present invention provides polymeric materials which are particularly suited for use as vehicles to gradually and continuously dispense active agents into the air, such as into a room atmosphere. The polymeric materials prepared in accordance with this invention avoid the disadvantages of previous proposals because, although they contain high levels of the active ingredient, they are clear, and to the extent desired, can be made flexible and tacky on the surface to permit their being easily and inconspicuously adhered to any convenient surface in a room, after which the active ingredient contained in the material is continuously and gradually released into the surrounding air. When the active agent is exhausted, the polymeric material can be readily removed and replaced with a fresh strip or sheet of the material. Alternatively, the clear polymeric materials of the invention can be made more rigid and can be tinted and/or molded into various three dimensional shapes to be sold in the form of decorative objects, such as pomanders, mobiles, artificial flowers and the like, or to be incorporated in such objects.

It is thus an object of the present invention to provide an improved polymeric material for release of active agents, such as air fresheners, room odorants, insecticides, insect repellants, and the like, which allows release of the active agent gradually over a period of time.

It is also an object of this invention to provide an active agent-containing polymeric material which can hold relatively large amounts of such active agents while remaining clear and transparent.

It is also an object to provide an improved room air freshener or similar active agent-containing polymeric material which can be made with sufficient tackiness to adhere to a wall or other surface without need for adhesive or a separate hanger.

It is a still further object to provide a polymeric material suitable as a vehicle for a room air freshener or similar active agents, which can be made with sufficient strength and flexibility to be capable of being formed into strips or other convenient forms, stored in rolled form if desired, and removed intact from a surface to which it has been applied when the active agent is depleted or no longer desired.

Further objects will become apparent from the following disclosure.

The invention provides polymeric compositions comprising synthetic polymerized hydroxyalkyl esters of vinylically unsaturated carboxylic acids, one or more volatilizable active ingredients, and a solublizing agent. The polymer backbone of the composition is preferably a cross-linked polymer of a hydroxyalkyl methacrylate or acrylate or a mixture thereof. In the principal application of the invention as a room air freshener, the active ingredient is a suitable fragrance oil or blend of fragrance oils. The solubilizing agent is an organic compound having both hydrophilic and lipophilic functions with HLB characteristics selected to substantially dissolve the active ingredients employed while itself being substantially dissolved in the polymer structure. (HLB values employed herein refer to the hydrophile-lipophile balance for measuring the hydrophilic and lipophilic tendencies of surfactants on a scale of 0 (completely lipophilic) to 20 (completely hydrophilic)).

The solubilizing agent permits useful amounts of active ingredient, including lipophilic blends of fragrance oils, perfumes and the like, to be incorporated in the polymer in a substantially dissolved state, thus permitting formation of a clear transparent resin which gradually releases the active ingredient into the atmosphere by volatilization at the surface. In addition, the solubilizing agent tends to loosen the structure of the polymer by interfering with hydrogen bonding of polar groups on proximate chains of the polymer, thereby increasing the mobility of the active ingredient from the interior to the surface of the resin, and to the extent desired, providing a softer resin. If a high loading or release rate of active ingredient is desired without softening the resin too greatly, the softening effect of the solubilizing agent can be compensated for by increasing the degree of cross-linking in the polymer structure.

In addition to the polymer matrix, active ingredient, and solubilizing agent, the compositions of the present invention preferably also include water, which tends to accelerate the volatilization of the active ingredient by co-evaporation. The water also serves as a vehicle for the catalyst systems preferred in preparing the compositions of the invention.

The compositions of the invention are preferably prepared by polymerizing the ingredients together with a peroxide or persulfate catalyst in combination with a reducing agent. Of the peroxide catalysts hydrogen peroxide is preferred because it leaves a residue of water, rather than odoriferous or otherwise objectionable inorganic residues, but persulfate catalysts, which also do not leave objectionable odors, can be used except in very low water systems containing insufficient water to dissolve the sulfate salts remaining. It is usually essential to employ a reducing agent, in combination with the primary catalyst, preferably a water soluble organic reducing agent, such as ascorbic or araboascorbic acid, in order to permit the polymerization to proceed rapidly while at temperatures which are low enough to avoid premature volatilization or degradation of the active ingredients. In systems containing sufficient water, inorganic reducing agents, such as sodium bisulfite can also be used.

The compositions of the invention can be molded into decorative objects or formed into sheets or strips and covered with release paper and/or sealed in a vapor retaining package to be stored until use. When the surface is exposed, the active ingredient begins to evaporate at the surface and is thereby released into the atmosphere. Further quantities of the active ingredient then begin to migrate to the surface in an ongoing equilibrating process within the polymer matrix, thereby providing a continuous and gradual release of the active ingredient over a sustained period.

For purposes of adhesive application, the tackiness of the polymer material at the surface can be controlled by varying the oxygen content of the polymerization atmosphere.

Where desired in the final product, the polymers may also be made to undergo visible changes. For example, indicators may be incorporated which change color, e.g., when the water content falls below a given level, or bilaminar strips may be made from polymers of differing water content which change shape by differential shrinkage. The former effect is useful to provide, for example, an indication of the degree of depletion of the active ingredient while the latter effect may be used, for example, in the construction of flowers whose petals open on standing.

DESCRIPTION OF THE PREFERRED EMBODIMENTS

Figure 1:
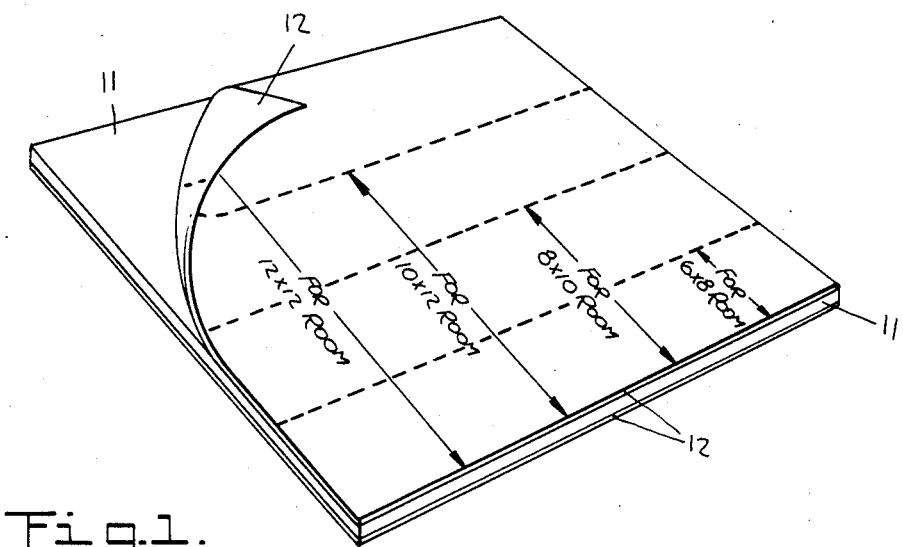
FIG. 1 depicts one form in which the active agent-containing polymeric material can be prepared with release paper on both sides of the polymeric sheet indicating sizes of polymeric strips to be used for release of the proper amount of active agent into rooms of different sizes.

The polymeric compositions of the present invention can be formed into a wide variety of products for gradual release of active ingredients into a room atmosphere. For example, they can be fabricated in the form of preshaped moderately flexible strips, discs or rectangles which are clear and tacky on the surface to permit their being inconspicuously adhered to surfaces such as walls, doors, door jambs and window frames and the like. This type of product permits a specific amount of active agent to be selected in direct relation to the volume and requirement of the room. Thus, for example, a square sheet may be provided, as shown in FIG. 1. The polymeric material, 11, is covered on both sides with an appropriate release paper 12. Patterns may be printed on the covering paper 12 indicating the size of sheet to be cut for specific room sizes. The paper plus polymeric product may then be cut with a pair of household scissors, and the paper then stripped away to provide the adherent sheet. Different size strips or squares may be cut from patterns on either side for several rooms from a single sheet.

Figure 2:
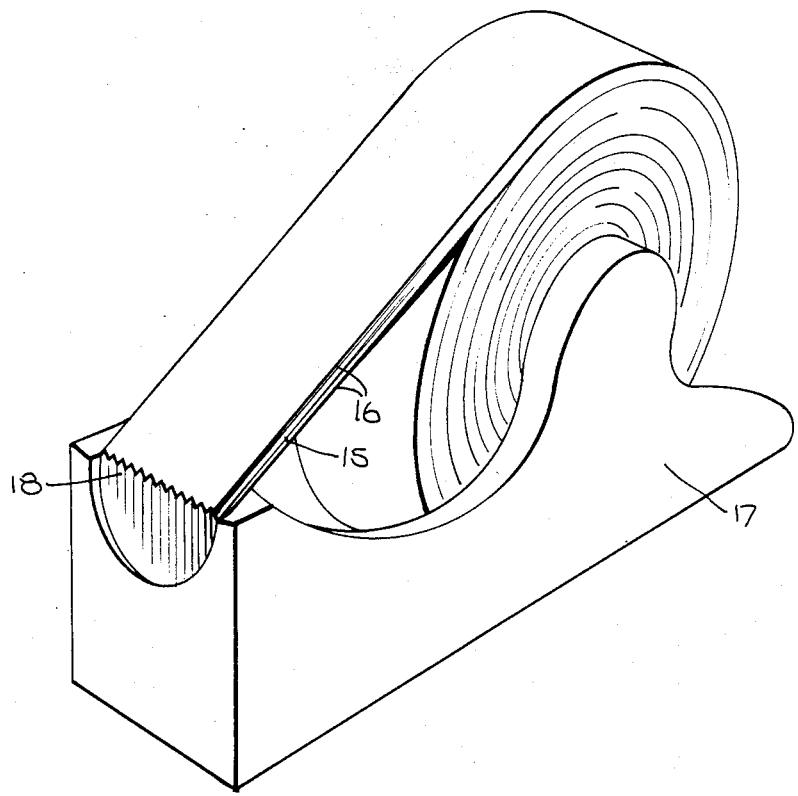
FIG. 2 depicts an alternative form for marketing the active agent-containing polymeric materials of the invention as a continuous strip, lined on both sides with release paper, and rolled on a strip dispenser with a sharp cutting edge.

Alternatively, the compositions of the invention may be made more flexible to permit their use in products stored in rolls. As shown in FIG. 2, the active agent containing polymeric material, 15, covered on each side with release paper, 16, may be supplied on a strip dispenser, 17, with a sharp cutting edge, 18. Accompanying instruction may indicate the desired size strip to be used for a given room area.

As a further alternative (not shown) which presently appears preferable from a consumer marketing standpoint in the case of fragrance release products, the compositions of the invention can be made substantially inflexible and non-tacky on the surfaces and molded into various decorative objects, such as flowers, birds, mobiles, pomanders and the like. For this purpose, the polymeric materials though clear are preferably dyed or tinted to give a stained or colored glass appearance.

As explained above the polymeric backbone of the compositions of the invention comprises polymerized hydroxyalkyl esters of vinylically unsaturated carboxylic acids, such as hydroxyalkyl methacrylates or acrylates or mixtures thereof. Typical monomers include hydroxyethyl acrylate, or preferably hydroxyethyl methacrylate, and the hydroxypropyl, hydroxybutyl and glyceryl esters of acrylic or methacrylic acid. Polyoxyalkylated derivatives of the foregoing monomers may also be used, such as polyoxyethylene acrylate or polyoxypropylene glyceryl monomethacrylate. Usually the number of oxyalkylene groups is up to 20 although higher alkoxylates are operative and may be preferred for certain specialized applications.

The compositions of the invention preferably contain cross-linking agents which have two or more vinylic functions. For example, ethylene glycol dimethacrylate or diacrylate are difunctional and may be used according to the invention, but because these dimers have no free hydroxyl functions, they are apt to be less compatible with the final product and are therefore less preferred than glyceryl diacrylate and dimethacrylate which also have two vinylic functions. Trifunctional cross-linking agents include glyceryl triacrylate, trimethylol propane triacrylate and preferably pentaerythritol triacrylate which is especially useful as a cross-linking agent. Tetrafunctional cross-linking agents, such as pentaerythritol tetraacrylate, can also be employed for greatest rigidity of the polymer compositions, since such agents have the potential for interacting with four polymer chains simultaneously. Alkoxylated derivatives of hydroxy containing cross-linking agents are also operative. Preferably, in the case of the preferred hydroxy alkyl methacrylate and acrylate monomers, the alkyl side chains should generally be no more than about five carbon atoms in length.

The polymer may optionally contain some non-hydroxylic monomers such as ethylmethacrylate or isobutylacrylate. Preferably, however the polymer contains at least 50% molar of hydroxyl groups or equivalent hydrophilic functionality based on the monomer, preferably at least 90%. For the purpose of this specification one hydroxyl group may be considered equivalent in hydrophilic functionality to four oxyethylene groups or six oxypropylene groups. The hydrophilic functionality may, to some extent, be varied according to the active ingredient, less highly hydrophilic polymers being preferred for highly lipophilic active ingredients, in order to provide greater compatibility.

The amount of cross-linking in the polymers of the invention may be chosen according to the degree of flexibility desired in the final product and the rate of release of the active ingredient required. The more highly cross-linked the polymer, the more rigid the polymer, and the lower will be the mobility of the active ingredient and the slower its rate of release. Conversely the lower the cross-linking, the more flexible the polymer and the more rapid the release of the active ingredient. Generally the polymeric compositions of the present invention have up to 20% cross-linking vinyl groups based on the number of monomer units, that is, a total of six vinylic groups for every five mols of monomer in the polymerizing mixture; e.g., one molecule of difunctional cross-linking agent per 10 monofunctional monomer molecules. The polymers of the invention may have no cross-linking if a very flexible material is desired. Preferably the amount of cross-linking is between about 1% and about 10%, where the percent cross-linking again refers to the percentage of cross linking vinylic groups.

The active ingredient may be any volatile or volatilizable substance which it is desired to release gradually over a sustained period into a room atmosphere in order to perform a useful function. The invention is particularly applicable to fragrances, including natural essential oils and synthetic perfumes and blends thereof. Typical examples of perfume compositions which may be used as, or more usually, as part of the active ingredient include derivatives of 2,6-dimethyl 2-alkoxyoctan-7-ol (as described in British Pat. No. 1,414,458), vetivert oil, vetiverol, vetiveryl acetate, guaiac wood oil, guaiac wood acetate, coumarin, musk ketone, lauric aldehyde, benzyl acetate, lemon oil, dimethyl benzyl carbinol, dimethyl benzyl carbinyl acetate, rose absolute, jasmin absolute, ionones, iso-nonyl acetate, methyl phenyl acetate, styrallyl acetate, β-phenyl ethanol, citronellol, citronellal, hydroxy citronellal, geranium oil, geraniol, linalool, nerol, lavandin oil, linalyl acetate, patchouli oil, petitgrain oil, bergamot oil, heliotropin, ethylene brassylate, undecyl aldehyde, cinnamaldehyde, benzyl salicylate, cinnamyl alcohol, clove bud oil, bay oil, nutmeg oil, pimento berry oil, terpineol, ylang oil, benzyl benzoate, sandalwood oil, clary sage oil, amyl salicylate, labdanum resin, methyl ionones, dihydromyrcenol, orange oil, vanillin, ethylvanillin, olibanum resin musk ambrette, rhodinol, mandarin oil, methyl nonyl acetaldehyde, neroli oil, cedrol, cedryl acetate, acetyl cedrene, oakmoss, isovalanone, eugenol, iso-eugenol, cedarwood oil, p-tert-butyl cyclohexyl acetate, amyl cinnamic aldehyde and hexyl cinnamic aldehyde. The active ingredients can also comprise blends of the foregoing, and in many cases will comprise at least five, often at least ten of the foregoing, and/or other, perfumery compounds and compositions.

Alternatively or additionally the active ingredient may comprise a volatile insecticide and/or insecticidal synergist, such as pyrethrum, or an active ingredient which is volatilized on heating, such as volatilizable fabric softeners of the type which may be volatilized when the resin is heated in, for example, a clothes drier, to soften fabrics therein.

The proportion of active ingredient may range from the minimum effective concentration, which will depend on the particular active ingredient, up to the maximum amount that can be incorporated in the resin, depending on the compatibility of the active ingredient with the polymer and the nature and amount of the solubilizing agent. It has been found possible, with some active ingredients to use amounts up to twice the amount by weight of the acrylic monomer. Other active ingredients may provide useful results in proportions as small as 100 ppm or even less. Typically, however, the proportion of active ingredient is between about 2% and about 50% by weight of the final composition; more preferably between about 5% and 20%.

The solubilizing agent is selected from among organic compounds having both hydrophilic and lipophilic functions, preferably from among non-ionic surfactants such as polyalkylene oxides, e.g., polyethylene oxide or polypropylene oxide having from 2 to 25 oxyalkylene units, or a polyoxyalkylene condensate with a fatty alcohol or alkyl aryl alcohol or with a glyceryl or sorbitol ester, or a polyoxyalkylene ester of a fatty acid. The solubilizing agent permits substantial amounts of the active ingredients, most of which in the case of fragrance oils are lipophilic, to be incorporated in the compositions of the invention in a substantially dissolved state so that the final product can be made clear and transparent. For this purpose, the particular solubilizing agent employed in a given composition is selected in accordance with the average polar characteristics of the active ingredients.

Typical examples of solubilizing agents include polyoxyethylene stearate, polyoxypropylene sorbitan monolaurate, polyoxyethylene glyceryl monooleate and polyoxyethylene nonyl phenyl ether. Glyceryl and sorbitan fatty esters themselves are similarly useful, as are the other commonly used non-ionic surfactants. In addition, small molecules having both hydrophilic and lipophilic functionality, hydroxyethylacetate, methyl hydroxyethyl ketone, methyl hydroxyethyl ether or propanediol can be used in certain applications where a volatile solubilizing agent is desired.

Selection of the optimum solubilizing agent depends on the nature of the active ingredient and the polar character of the resin. The solubilizing agent is chosen according to its HLB value so as to be compatible with the active ingredient and with the polymer matrix. Thus, for highly lipophilic active ingredients it is desirable to employ the more lipophilic solubilizing agents, and preferably, to make the polymer more lipophilic in character by lowering the proportion of hydroxyl groups, or to use a mixture of a relatively lipophilic and a relatively hydrophilic solubilizing agent.

Although non-ionic solubilizing agents are strongly preferred, it is sometimes possible or advantageous to use an ionic surfactant, at least as part of the solublizing agent. Preferably such ionic solubilizing agents are cationic, such as quaternary ammonium salts, betaires or imidazolines.

The proportion of the solubilizing agent can range from about 5% to about 40% by weight of the final composition, preferably from about 10% to 25%. The amount of solubilizing agent in a given formulation will depend on the requirements of the system, including the relative compatibility of the active ingredient and the acrylic monomer, the amount and release rate of the active ingredient to be incorporated in the composition, and the desired flexibility or rigidity of the product. Large amounts of solubilizing agent tend to render the product more flexible, and to increase the capacity for active ingredient and its release rate, while maintaining the active ingredient in a substantially dissolved state to form a clear and transparent polymeric material.

In addition to the acrylic polymer backbone, the active ingredients, and the solubilizing agent, the compositions of the invention optionally contain water. The presence of at least some water is generally desirable as a vehicle for the catalyst systems preferably used in preparing the compositions of the invention. However, with some catalysts it has been found possible to prepare substantially anhydrous polymers. The presence of water tends to accelerate the volatilization of the active ingredient by co-evaporation and is, therefore, often desirable in amounts up to the maximum capacity of the system, which in practice is usually about 50% by weight of the polymer composition. Typically the amount of water is between 1 and 40% by weight of the composition. In addition, because of the hydrophilic character of the hydroxy alkyl acrylic monomers employed in the polymer matrix, the proportion of water influences the dimensional stability of the polymer. A high proportion of water will result in shrinkage of the polymer composition as the water evaporates. Low proportions of water provide dimensionally more stable compositions.

The polymeric compositions of the invention are prepared by mixing together the monomer, solubilizing agent and active ingredient, together with any cross-linking agent and water to be employed in the given formulation and, preferably, the primary catalyst in combination with the reducing agent. Although the mixture may polymerize without a catalyst if allowed to stand for long periods of time or if heated to temperatures which are apt to exceed the volatilization or decomposition temperatures of most fragrance oils employed as active ingredients, it is generally necessary to use a catalyst.

One problem with polymers of the type employed in the present invention, is the elevated temperature normally required to initiate polymerization in a commercially acceptable time. Together with the heat released during the exothermic polymerization reaction, this can result in premature volatilization of active ingredients or degradation of the heat sensitive material. Accordingly, for most active ingredients, particularly many of the fragrance oils, it is necessary to use a combination of a peroxide catalyst and a reducing agent as an initiator. Typical peroxide catalysts which may be used include benzoyl peroxide, hydrogen peroxide, hexanoyl peroxide, isobutyl peroctoate, the commercial catalyst known as Lupersol 256 (2,5-dimethyl-2,5-bis(2-ethyl hexanoyl peroxy)hexane), potassium persulfate and ammonium persulfate. The persulfate catalysts should only be used in systems containing sufficient water to dissolve the sulfate residue in the finished product. Hydrogen peroxide is particularly preferred because it leaves only water as a residue. Some organic peroxide catalysts, such as Lupersol 256, are frequently less preferred because they leave odoriferous or otherwise objectionable residues.

Organic reducing agents, such as ascorbic acid, and araboascorbic acid are preferred as initiators, although in systems containing sufficient water to dissolve the residue, inorganic reducing agents, such as sodium bisulfite, can also be used.

It has been found that the combination of hydrogen peroxide or persulfate catalysts with organic water soluble reducing agents, such as ascorbic and araboascorbic acid, permits polymerization in commercially acceptable times at temperatures of about room temperature and below. Where the equipment is available and time permits, it is also possible to polymerize at room temperature using those reducing agents with UV catalysts.

The peroxide catalyst can be used in amounts up to about 1% of the final composition, but is preferably used in amounts from about 0.1% to about 0.5%. The reducing agent can be employed in amounts up to 3% of the final composition, but is preferably used in amounts from about 0.2% to 1.5%.

Although methacrylates are preferred as the basic monomer because they lack residual odor, the rate of polymerization can be increased by using high molecular weight acrylate cross-linking agents, since acrylates tend to polymerize more readily at lower temperatures.

It is preferable that the reactants be cooled prior to use. If the reactants are at room temperature when mixed, it is possible that the polymerization reaction may begin prior to depositing the solution into the appropriate molds. Generally, it is sufficient to cool the reactants to the range of ordinary refrigerator temperature, or about 0° C., to about 5° C. The mold is then allowed to set at an initial temperature of about 0° C. to about 50° C., and preferably 5° C. to about 35° C., for about 1 minute to about 4 hours, preferably from about 10 minutes to about 1 hour. The exothermic reaction may raise the temperature as high as about 70° to 80° C. for a brief period.

The polymerization reaction is preferably effected under an inert atmosphere of, for example, carbon dioxide or nitrogen, or under tight sealing films to avoid inhibition of polymerization at the surface by oxygen. However, to make the self-adhesive embodiments of the invention, oxygen is introduced to make the polymeric composition tacky at the surface. The degree of surface tack can be controlled through variation of the partial pressure of oxygen in the polymerization environment. The greater the oxygen, the greater the potential surface tack. In addition to the use of inert gaseous diluents, such as carbon dioxide and nitrogen, to reduce the oxygen content of the surrounding environment to a predeterminable level, the chamber can be partially evacuated, although too great an evacuation may lead to excessive evaporative loss of the dissolved volatile active agents. Reducing the temperature of the polymerization minimizes such loss.

EXAMPLE I

Self-adhesive Disk

Mix 81.4 mg. of ascorbic acid with 12.5 ml. of hydroxyethyl methacrylate, 9.8 ml. of polyethyleneglycol (MW 400), and 1.5 ml. of rose oil concentrate. Separately dissolve 0.125 gm. of potassium persulfate in 6 ml. of water, and then mix the two solutions quickly. Pour the liquid into a cylindrical dish to a ¼" height, and place in a vacuum chamber at a pressure of 7 in. of mercury and a temperature of 25° C. After 30 minutes the polymerized disc, containing 5% rose oil, is removed. It is clear, colorless, and has a surface tack.

EXAMPLE II

Non-adhesive Disk

Mix 40.7 mg. of erythorbic acid with 12.5 ml. of hydroxypropylmethacrylate, 9.8 ml. of polyethylene glycol (MW 400) and 7.1 ml. of rose oil in an ice bath. Separately mix 62.5 mg. of potassium persulfate in 6 ml. of water, cool in an ice bath, and mix the two solutions. Precool a cylindrical plate to 0° C., pour in the liquid mixture to a height of ¼", and place the plate in an ice bath under a carbon dioxide atmosphere. Remove the plate in one hour, to obtain a non-tacky disc containing 20% rose oil.

EXAMPLE III

Self-adhesive Disk

Mix 40.7 mg. of d-araboascorbic acid with 9.8 ml. of polyethylene glycol (MW 600), 6.2 ml. of hydroxyethyl methacrylate, 6.2 ml. of glycidyl methacrylate, and 3.1 ml. of a mixed-floral odor oil. Cool in an ice bath. Mix in a precooled mixture of 62.5 mg. of potassium persulfate in 6.0 ml. of water, and pour into precooled cylindrical plates to a height of ¼". Place the dishes in an ice bath under a low oxygen nitrogen enriched atmosphere and allow to cure for 45 minutes. The resulting discs are clear, tacky, and contain 10% of the fragrance oil.

EXAMPLE IV

Self-adhesive Sheet

Mix 0.107 gm. of ascorbic acid, 12 ml. of water, 25 ml. of hydroxyethyl methacrylate, 19.6 ml. of polyethylene glycol (MW 400), and 0.25 ml. of initiator 2,5-dimethyl-2,5-bis(2-ethyl hexanoyl peroxy)hexane. Heat the mixture to 50° C., with stirring, until the mixture begins to thicken, and then stir in 6.3 ml. of pine oil. Pour the mixture into a rectangular mold to a height of ¼" and place in a carbon dioxide atmosphere at room temperature to solidify. In 1 hour remove the cured sheet, containing 10% pine oil, and place between two pieces of release paper.

EXAMPLE V

Self-adhesive Strip

Mix 0.43 gm. of erythorbic acid, 100 ml. of water, 100 ml. of hydroxypropyl methacrylate, 78.5 ml. of polyethylene glycol (MW 400), 10 ml. of distilled spearmint oil, and 1 ml. of the UV catalyst "Trigonal 14". Pour into a rectangular plate to a height of ¼" and irradiate, in a low oxygen nitrogen enriched atmosphere, with long-wave ultraviolet light at room temperature. After 4 hours remove the sheet, containing 3.5% odorant, cut 1-inch wide strips, place between 1-inch wide 1-mil polyethylene strips, and roll onto a "scotch-tape" tape roll dispenser.

EXAMPLE VI

The procedure of Example II is repeated using 7.1 ml. of citronella oil instead of the rose oil. This produces a non-tacky disc suitable for use as an insect repellant.

EXAMPLE VII

The procedure of Example II is repeated with 0.25 ml. of ethylene glycol dimethacrylate added to the hydroxy propyl methacrylate monomer. This produces a product having a stiffer texture and slower release rate than the product of Example II because of the additional cross-linking introduced.

EXAMPLE VIII

Molded Duck

Mix 20 ml. of HEMA, 80 ml. of nonylphenoxy polyoethoxyethanol (HLB ratio 8.8), 5 ml. of ethyleneglycol dimethacrylate, and 10 ml. of cinnamic aldehyde with 418 mg. of ascorbic acid dissolved in 5 ml. of water. Then stir in 320 mg. of ammonium persulfate dissolved in 15 ml. of water. Add 1 drop of brown aqueous dye and pour the mixture into a two-part plaster mold of a duck, cover the base with a sheet of Saran and allow to set for 30 minutes. Remove the transparent tan product, which contains 5% dissolved fragrance.

EXAMPLE IX

Stained Glass Mobile

Mix 58.6 gms. of hydroxypropyl methacrylate, 26.1 gms. of alkylphenoxy polyethoxyethanol (HLB 14), 3.4 gms. of pentaerythritol triacrylate, 10 gms. of strawberry fragrance oil, and one drop of oil-soluble red dye. Mix in 1.3 gms. of a warm 50:50 solution of ascorbic acid in water, then 0.3 gms. of 35% hydrogen peroxide, and finally 0.2 gms. of conc. hydrochloric acid. Pour into a 3/16" deep thermoform mold containing a form-fitting metal frame in the shape of a strawberry. Cover with an air-impermeable sheet of plastic and let cure for 5 minutes. Remove the cured product, containing less than 0% moisture, from the thermoform mold, to obtain a hangable, metal-framed transparent red mobile, which has the appearance and aroma of a strawberry. During use, over a period of several months, as the 10% fragrance oil slowly evaporates, the product shows no cracking or detectable shrinkage of polymer material away from the metal frame, as would be evident in a product with significantly higher water content (over about 5%).

EXAMPLE X

Indicating Polymer

Mix 24 ml. of hydroxypropyl methacrylate, 7 ml. of nonylphenoxy polyethoxyethanol (HLB 12.5), 3 ml. of pentaerythritol triacrylate, 5.8 ml. of rose fragrance oil, 1 ml. of a 14% aqueous solution of cobalt chloride hexahydrate, 13 ml. of water, and 2.5 ml. of a 23% aqueous solution of ascorbic acid. Quickly mix in 1.3 ml. of 3% hydrogen peroxide and 0.1 ml. of conc. hydrochloric acid, pour into a petri dish, and place in a nitrogen chamber. The resulting pink product contains 10% fragrance and 30% water. As the water and fragrance co-evaporate over a period of time the water and fragrance contents will reach a point of depletion (at about 5% water) that the disc will become a bright blue (from the dehydration of the cobalt salt).

EXAMPLE XI

Molded Cherries

Mix 264 ml. of HEMA, 168 ml. of a polyoxyethylene (10) polyaryl phenol, 6 ml. of ethyleneglycol dimethacrylate, and 65 ml. of cherry fragrance oil. To this add a solution of 1.1 gms. of erythorbic acid in 24 ml. of water followed by 0.85 gms. of ammonium persulfate in 120 ml. of water containing red dye. Pour quickly into spherical glass molds (ca. 40 ml. capacity) and insert 1" plastic stems half-way into each liquid. Place the molds in an oxygen-free, carbon dioxide environment, and let cure for 30 minutes. Remove the clear, molded cherries containing 10% cherry fragrance and 22% water, by breaking each glass mold.

EXAMPLE XII

Shrinking Disc

Mix 25 ml. of HEMA, 9.8 ml. of 2-methoxyethanol, 8.4 ml. of propylene glycol, 7.6 ml. of 2-hydroxyethyl acetate, 0.25 ml. of ethyleneglycol dimethacrylate, and 19 ml. of rose oil fragrance. Stir in a solution of 0.13 gms. of ascorbic acid in 1 ml. of water followed by 0.1 gms. of ammonium persulfate in 2 ml. of water. Pour into a dish and cover with an oxygen-barrier film. After 1 hour remove the disc, which contains 25% fragrance oil and a total of 42% volatile fragrance oil carriers (including water) which evaporate at different rates. The three organic carriers are characterized by having lipophilic and hydrophilic functionality. Upon full evaporation of all volatiles, the disc shrinks to one third its original size.

EXAMPLE XIII

Bilaminar Star

Mix 12.5 ml. of HEMA, 9.8 ml. of nonylphenoxy polyethoxyethanol (HLB 13.0), 0.25 ml. of pentacrythritol tetraacrylate, and 14.8 ml. of honeysuckle fragrance oil, with 0.13 gms. of ascorbic acid dissolved in 2 ml. of water. Then stir in 0.10 gms. of ammonium persulfate dissolved in 10 ml. of water and add 1 drop of aqueous green dye. Half fill a star-shaped mold with the mixture, and let cure for 20 minutes, uncovered. Onto this, pour the following mixture: 12.5 ml. of HEMA, 9.8 ml. of nonylphenoxy polyethoxyethanol (HLB 13.0), 0.13 ml. of ethyleneglycol dimethacrylate, 14.8 ml. of honeysuckle oil. 0.13 gms. of ascorbic acid in 2 ml. of water, 0.10 gms. of ammonium persulfate in 20 ml. of water and 1 drop of aqueous green dye. Cover with Saran and let set. The resulting bilaminar star, when removed, will slowly curl up with time as the fragrance oil and water slowly evaporate to different degrees over a several week period. (One side of the star contains 30% fragrance oil and 24% water, the other contains 25% oil and 37% water).

EXAMPLE XIV

Fragrance Hand Conditioner in Sponge

Mix 10 ml. of hydroxypropyl methacrylate, 5 ml. of nonylphenoxy polyethoxyethanol (HLB 8.8), 0.25 ml. of pentaerythritol triacrylate, 2.4 ml. of honeysuckle fragrance oil, 5 ml. of isopropyl myristate, and 0.9 ml. of a 23% aqueous solution of ascorbic acid. To this add 0.1 ml. of 35% hydrogen peroxide and 0.05 ml. of conc. hydrochloric acid, mix pour into a 3½" diameter petri dish, and cover with a sheet of Saran. Remove the disc, which contains 10% fragrance oil and 21% isopropyl myristate oil, and cut ½×1" strips for insertion into slits in the center of household sponges (cellulose or polyurethane foam). During use, when the sponges are wet, they release a pleasant fragrance and the skin-soothing oil isopropyl myristate.

EXAMPLE XV

Molded Soap Dish

Mix 57 ml. of hydroxypropyl methacrylate, 26 ml. of nonylphenoxy polyethoxyethanol (HLB 12.5) 2.7 ml. of pentacrythritol triacrylate and 11 ml. of lilac fragrance oil. Add 4.4 ml. of a 23% aqueous solution of ascorbic acid, stir, add 1 drop of aqueous crystal violet solution and 0.48 ml. of 35% hydrogen peroxide. Stir, add 5 drops of conc. hydrochloric acid, mix quickly, pour into a soap dish mold, and cover with Saran film. The resulting product, after 10 minutes of polymerizing and cooling, is optically clear and hard, with randomly distributed internal cracks (resulting from the relatively high level of cross-linking). It contains 2.4% water and 11% fragrance oil. When employed as a soap dish, excess water from freshly-used soap causes the dish to partially hydrate, and the subsequent evaporation of absorbed moisture "boosts" the lilac fragrance above its normal evaporation rate.

EXAMPLE XVI

Humidity Sensitive Disc

Mix 25 ml. of HEMA, 20 ml. of nonylphenoxy polyethoxyethanol (HLB 12.5), 0.50 ml. of ethyleneglycol dimethacrylate, 14.2 ml. of lavender oil and 1 gm. of calcium chloride (anhydrous) in 8 ml. of water. Stir in 0.13 gm. of ascorbic acid dissolved in 2 ml. of water, followed by 0.1 gm. of ammonium persulfate in 2 ml. of water and a drop of violet dye. Pour the mixture into a thermoform flower mold and cover with an oxygen-impervious film. This sample is responsive to relative humidity in its environment. After some of its contained moisture co-distills with the dissolved 20% fragrance oil, the product attains a composition whereat above ambient relative humidities of ca. 35–40% the product absorbs moisture from the environment, which moisture then co-distills with fragrance oil as the humidity drops to give a "boost" to the normal evaporation rate of the fragrance oil. This "moisture-pump" effect can repeat itself during the effective life of the product.

EXAMPLE XVII

Molded Oak Leaf

Mix 16 ml. of hydroxypropyl methacrylate (HEMA), 3 ml. of octylphenoxy polyethoxyethanol (HLB 12), 1 ml. of pentaerythritol triacrylate, and 2.42 ml. of "early spring" fragrance oil. To this add a solution of 300 mg. of ascorbic acid in 1 ml. of water, mix, then 1 ml. of 3% hydrogen peroxide and 1 drop of aqueous green dye. Mix quickly and add one drop of conc. hydrochloric acid, stir, and pour into a thermoform leaf-shaped mold (¼" thick). Cover with air-impermeable plastic film, and let cure. The product can be removed in 5 minutes from the mold, or allowed to cool for another 5 minutes before removal. It is transparent and stiff, contains 10% fragrance and 8% water, and is suitable for insertion in an appropriate stand-up frame as a room odorizer.

EXAMPLE XVIII

Molded Chick

Mix 65 ml. of HEMA, 67 ml. of nonylphenoxy polyethoxyethanol (HLB ratio 12.5) 3.1 ml. of ethyleneglycol dimetharcylate, and 37.5 ml. of rose fragrance oil with 340 mg. of ascorbic acid dissolved in 2.6 ml. of water. Then stir in 260 mg. of ammonium persulfate dissolved in 12 ml. of water. Pour this clear mixture into a silicone rubber chick mold, and cover the liquid with a 1 mil. thick sheet of polyvinylidene chloride (Saran) and let cure for 20 minutes. Remove the resulting product from the mold, to obtain a solid transparent chick which contains 20% of rose fragrance oil.

What is claimed is:

1. A solid shape-retaining room air dispensing product for gradually dispensing a volatilizable fragrance into a room atmosphere comprising:
    a cross-linked polymer of a hydroxypropyl methacrylate or hydroxyethyl methacrylate monomer and a cross-linking agent of pentaerythritol triacrylate, the cross-linking agent being present at from about 1 to about 10 weight percent relative to the weight of the monomer;
    in combination with from about 5 to about 20 weight percent, relative to the total weight of the product, of a volatilizable, lipophilic active fragrance which has not been prematurely volatilized or degraded during polymerization of the monomer and cross-linking agent, and from about 10 to 25 weight percent, relative to the total weight of the product, of a nonionic surfactant of nonylphenoxypolyethoxyethanol, the nonionic surfactant having an HLB ratio between about 8.8 and 14 and having hydrophilic and lipophilic functions selected to dissolve or disperse the active fragrance in the polymer;
    the weight percentage of monomer present in the product being essentially 100 percent less the weight percentages of cross-linking agent, active fragrance and nonionic surfactant;
    the cross-linked polymer being a matrix in which the active fragrance is dispersed by the nonionic surfactant;
    the product being substantially free from other ingredients, being substantially clear, being substantially shape retaining, being substantially inflexible, and allowing sustained release of the active fragrance into the atmosphere.

2. A solid, shape retaining room air dispensing product according to claim 1 wherein the monomer present in the polymer is hydroxypropyl methacrylate.

3. A solid, shape retaining room air dispensing product according to claim 1 wherein the monomer present in the polymer is hydroxyethyl methacrylate.

* * * * *